(12) United States Patent
Oyaski

(10) Patent No.: US 6,596,917 B2
(45) Date of Patent: Jul. 22, 2003

(54) DEVICE AND METHOD FOR CLOSING MINOR CUTS WHICH WOULD NORMALLY REQUIRE STITCHES

(76) Inventor: Michael F. Oyaski, 207 E. Highland Ave., Ebensburg, PA (US) 15931

( * ) Notice: Subject to any disclaimer, the term of this patent is extended or adjusted under 35 U.S.C. 154(b) by 18 days.

(21) Appl. No.: 09/928,786

(22) Filed: Aug. 13, 2001

(65) Prior Publication Data

US 2003/0032910 A1 Feb. 13, 2003

(51) Int. Cl.⁷ ................................................ A61F 13/00
(52) U.S. Cl. .................... 602/43; 602/48; 606/215; 606/216; 128/887; 128/888
(58) Field of Search ............... 602/41–47, 48; 128/887, 888; 606/215, 216

(56) References Cited

U.S. PATENT DOCUMENTS

| | | | | |
|---|---|---|---|---|
| 3,991,754 A | * | 11/1976 | Gertzman | 604/387 |
| 5,086,763 A | * | 2/1992 | Hathman | 602/42 |
| 5,176,703 A | * | 1/1993 | Peterson | 606/216 |
| 5,234,462 A | * | 8/1993 | Pavletic | 606/215 |
| 5,445,597 A | * | 8/1995 | Clark et al. | 602/48 |
| 5,843,025 A | * | 12/1998 | Shaari | 602/53 |
| 5,947,998 A | * | 9/1999 | Cartmell et al. | 606/213 |
| 6,007,564 A | * | 12/1999 | Haverstock | 606/216 |
| 6,164,279 A | * | 12/2000 | Tweedle | 128/888 |
| 6,329,564 B1 | * | 12/2001 | Lebner | 602/41 |

* cited by examiner

Primary Examiner—Nicholas D. Lucchesi
Assistant Examiner—Lalita M. Hamilton

(57) ABSTRACT

A device for closing and promoting the healing of a skin laceration in a predetermined skin portion of the body. The device comprising a first means engageable with a skin portion of the body for drawing such laceration together. A screen member disposed intermediate with the skin laceration and first means for maintaining closure of such skin laceration. A medical adhesive engageable with a screen member as a means for sealing the skin laceration together.

12 Claims, 1 Drawing Sheet

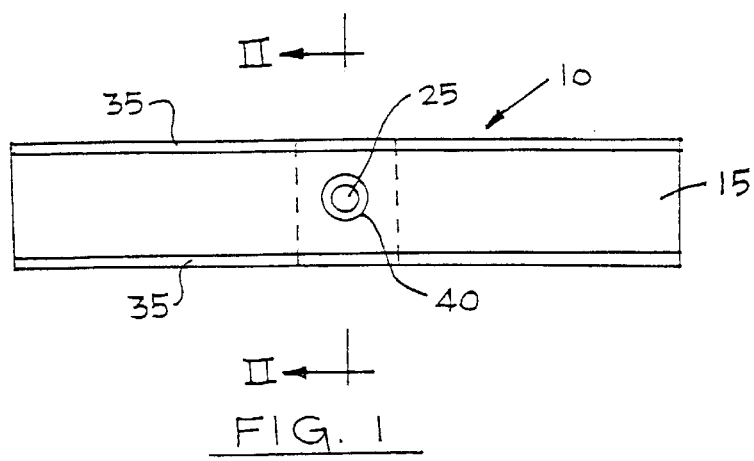
FIG. 1
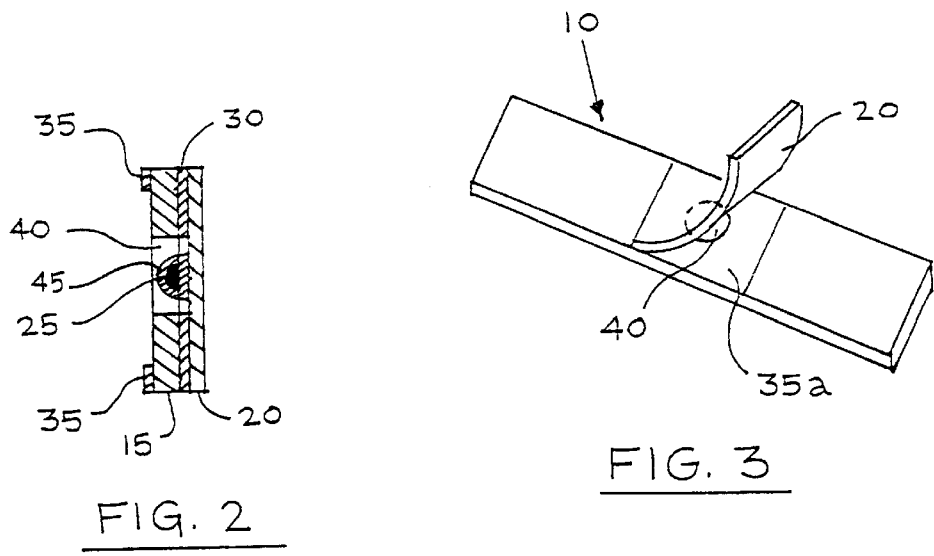
FIG. 2
FIG. 3

DEVICE AND METHOD FOR CLOSING MINOR CUTS WHICH WOULD NORMALLY REQUIRE STITCHES

FIELD OF THE INVENTION

The present invention relates, in general, to relatively small cuts in a portion of the body and, more particularly, this invention relates to a device and method for closing the skin without the use of stitches.

BACKGROUND OF THE INVENTION

Prior to the present invention, as is well known people are susceptible to various cuts. Some of these cuts may be serious enough to require medical attention and stitches. Because these cuts are open wound on the skin, they are often painful and sometimes bleed. It is also possible that due to there location they may be slow to heal because they can be exposed to water, air, detergents, and other external elements. A bandage is sometimes used, but this acts merely as a cover which affords minimal protection from the above mentioned elements.

SUMMARY OF THE INVENTION

In a first aspect, the present invention provides a device for promoting the healing of a laceration in a predetermined skin portion of the body. The device includes a first means engageable with the skin portion of the body for drawing the laceration together. A screen member attached to the first means and disposed intermediate with the skin laceration and the first means. Finally, a medical adhesive engageable with the screen member is used for sealing the laceration.

In a further aspect, the present invention provides a method for promoting the healing of a skin laceration. Such method comprises the steps of positioning the device and the screen member attached to an aperture in the device over the laceration. The laceration is closed by securing the device to the skin. A predetermined amount of medical adhesive is applied through the aperture. The medical adhesive is allowed to dry, and then the device is removed. The screen member and the medical adhesive remain attached to the closed stress crack for a predetermined amount of time, whereby the laceration will be healed.

OBJECTS OF THE INVENTION

It is therefore a primary object of the present invention to provide a device for promoting the healing of relatively minor skin lacerations without requiring the use of stitches or staples.

It is a further object of the present invention to provide a method for an individual to effectively treat a laceration to the skin without assistance, since at least one hand is free to apply the application of the medical adhesive once the device is secured on the skin.

Still a further object of the present invention is to minimize the discomfort associated with an open laceration during the healing process.

In addition to the various objects of the invention that have been described above, various other objects and advantages of the invention will become more readily apparent to those persons skilled in the relevant art from the following more detailed description of the invention, particularly, when such description is taken in conjunction with the attached drawing figures and the appended claims.

BRIEF DESCRIPTION OF THE DRAWINGS

FIG. 1 is a top view of a device for closing and promoting the healing of a laceration in the skin;

FIG. 2 is a partial sectional view taken along line II—II of FIG. 1; and

FIG. 3 is a bottom perspective view of a device for closing and promoting a laceration in the skin.

BRIEF DESCRIPTION OF A PRESENTLY PREFERRED AND VARIOUS ALTERNATIVE EMBODIMENTS OF THE PRESENT INVENTION

Prior to proceeding to a more detailed description of the invention, it should be noted that identical components having identical functions have been designated with identical reference numerals throughout the several views illustrated in the drawings for the sake of clarity.

Now refer more particularly to FIGS. 1, 2, and 3 of the drawings. Illustrated therein is a device, generally designated 10, for closing and promoting the healing of a topical laceration. The device 10 includes a first means 15 engageable with a skin portion of the body for drawing the lacerated skin together. The first means 15 is an adhesive element having a predetermined material, size, and shape. The first means 15 further includes an aperture 40 of a predetermined size and shape disposed through the first means 15. The first means 15 includes at least one reinforcement member 35 to prevent any material deformation of such first means 15. The reinforcement member 35 is disposed longitudinally along and engageable with such first means 15. Preferably, the device 10 includes two reinforcement members 35. An alternative embodiment includes one reinforcement member 35a disposed adjacent the circumference of the aperture 40 and engageable with such first means 15.

The device 10 further includes a screen member 20 disposed intermediate the skin laceration and the first means 15 for maintaining closure of the skin. The screen member 20 is a permeable, transparent, degradable material of a predetermined composition. The screen member 20 is attached to and overlaps the aperture 40 of such adhesive element 15 by an adhesive 30.

Included further in the device 10 is a medical adhesive 25 engageable with the screen member 20 as a means for sealing such skin laceration together without the use of stitches. Preferably, the medical adhesive 25 is contained in an encapsulated unit 45 having a predetermined amount of such medical adhesive 25.

Further described herein is a method for closing and promoting the healing of a relatively minor skin laceration without the use of staples and/or stitches. The method includes the positioning of an adhesive element with a screen member and a liquid or fluid encapsulated unit of medical adhesive attached to an aperture over such laceration. Securing the adhesive element to the skin to close the laceration. The method further includes pressing the first end of the adhesive element to the skin, then pulling the second end of the adhesive element until the laceration is closed. Pressing the second end of the adhesive element to the skin maintains closure of the laceration.

A predetermined amount of medical adhesive is applied by releasing the encapsulated unit of medical adhesive through such aperture. Preferably, the medical adhesive is released through the aperture by applying pressure to the encapsulated unit. The medical adhesive is allowed to dry, then the adhesive element is removed. The screen member and the medical adhesive remain attached to the closed laceration for a predetermined amount of time. An additional step includes trimming the screen member to fit such skin portion of the body. Preferably, the screen member is composed of a degradable material. After the predetermined amount of time has lapsed, the laceration will be healed.

Although the invention has been shown in connection with a certain specific embodiment, it will be readily apparent to those skilled in the art that various changes in form and arrangement of parts and method may be made to suit requirements without departing from the spirit and scope of the invention.

I claim:

1. A device for closing and maintaining closed a relatively minor laceration in a predetermined skin portion of a human body in order to promote healing of such laceration, said device comprising:
    (a) an elongated first means having an adhesive layer disposed on one side thereof, a first predetermined portion of such adhesive layer is engageable with such skin portion of such human body adjacent one side of such laceration to enable drawing such laceration together and a second predetermined portion of such adhesive layer engageable with such skin portion adjacent an opposed side of such laceration to enable maintaining such laceration in such skin portion substantially together for a period of time which is at least sufficient to prevent reopening of such laceration;
    (b) an aperture formed substantially in a center of said elongated flexible first means;
    (c) at least one reinforcement member engageable with said elongated first means at least adjacent said opening for preventing deformation of said opening;
    (d) a screen member having a predetermined size and a predetermined shape disposed intermediate such skin laceration and a predetermined portion of said adhesive layer disposed on said one side of said first means for maintaining closure of such skin laceration upon removal of such elongated first means; and
    (e) a medical adhesive engageable with said screen reinforcing member and said predetermined skin portion as a means for sealing such skin laceration together.

2. The device, according to claim 1, wherein said at least one reinforcement member is disposed longitudinally along said first means.

3. The device, according to claim 2, wherein said device includes a pair of reinforcement members disposed longitudinally along said first means adjacent each outer edge thereof.

4. The device, according to claim 1, wherein said at least one reinforcement member is disposed adjacent a circumference of said aperture and engageable with said first means.

5. The device, according to claim 1, wherein said screen member comprises a permeable, transparent, degradable material of a predetermined composition.

6. The device, according to claim 1, wherein said screen member is attached to and overlaps said aperture of said adhesive element.

7. The device, according to claim 1, wherein said medical adhesive is an encapsulated unit of a predetermined amount of medical adhesive.

8. A method of closing and promoting healing of a skin laceration without use of at least one of stitches and staples, said method comprising the steps of:
    (a) positioning an adhesive element with a screen member and a fluid encapsulated unit of medical adhesive attached to an aperture over a laceration occurring in a predetermined skin location;
    (b) closing such laceration by securing said adhesive element to said skin;
    (c) applying a predetermined amount of medical adhesive by to said laceration by releasing said unit of medical adhesive through said aperture;
    (d) allowing said medical adhesive to dry;
    (e) removing said element, wherein said screen member and said medical adhesive remain attached to the closed laceration for a predetermined amount of time, whereby said laceration will be healed.

9. A method for closing and promoting healing of a skin laceration, according to claim 8, wherein step (b), in said method is accomplished by pressing a first end of said element to said skin, pulling a second end of said element until such laceration is closed, and pressing said second end of said element to said skin to maintain closure of said laceration.

10. A method for closing and promoting healing of a skin laceration, according to claim 9, wherein step (c), in said method is accomplished by applying pressure to said encapsulated unit to release said medical adhesive.

11. A method for closing and promoting healing of a skin laceration, according to claim 9, wherein step (e) in said method further includes the additional step of trimming said screen member to fit such skin portion of the body.

12. A method for closing and promoting the healing of a skin laceration, according to claim 9, wherein step (e), in said method further includes the use of degradable material for said screen member.

* * * * *